United States Patent
Tian et al.

(10) Patent No.: US 8,410,098 B2
(45) Date of Patent: Apr. 2, 2013

(54) N-{1-[3-(2-ETHOXY-5-(4-ETHYLPIPERA ZINYL)SULFONYLPHENYL)-4,5-DIHYDRO-5-OXO-1,2,4-TRIAZIN-6-YL]ETHYL} BUTYRAMIDE, THE PREPARATION METHOD AND USE THEREOF

(75) Inventors: Guanghui Tian, Shanghai (CN); Zheng Liu, Shanghai (CN); Jin Zheng, Shanghai (CN); Jingshan Shen, Shanghai (CN)

(73) Assignee: Topharman Shanghai Co., Ltd., Shanghai (CN)

( * ) Notice: Subject to any disclaimer, the term of this patent is extended or adjusted under 35 U.S.C. 154(b) by 188 days.

(21) Appl. No.: 12/810,898

(22) PCT Filed: Dec. 28, 2007

(86) PCT No.: PCT/CN2007/003872
§ 371 (c)(1),
(2), (4) Date: Sep. 1, 2010

(87) PCT Pub. No.: WO2009/082845
PCT Pub. Date: Jul. 9, 2009

(65) Prior Publication Data
US 2011/0190495 A1  Aug. 4, 2011

(51) Int. Cl.
C07D 253/065 (2006.01)
C07D 253/00 (2006.01)
C07D 487/04 (2006.01)
A61K 31/53 (2006.01)
A61P 15/10 (2006.01)

(52) U.S. Cl. ......... 514/242; 514/243; 544/182; 544/184

(58) Field of Classification Search .............. 544/182, 544/184; 514/242, 243
See application file for complete search history.

(56) References Cited

U.S. PATENT DOCUMENTS

| | | | |
|---|---|---|---|
| 6,362,178 B1 * | 3/2002 | Niewohner et al. | 514/218 |
| 2006/0264624 A1 | 11/2006 | Heim-Riether et al. | |
| 2012/0088769 A1 * | 4/2012 | Ly | 514/237.2 |

FOREIGN PATENT DOCUMENTS

| CN | 1437589 A | 8/2003 |
|---|---|---|
| WO | WO 99/24433 | 5/1999 |
| WO | WO 02/50075 A1 | 6/2002 |
| WO | WO 02/50076 A2 | 6/2002 |

OTHER PUBLICATIONS

International Search Report for Appln. No. PCT/CN2007/003872 dated Oct. 9, 2008.
Riether et al., "A Novel Method for the Synthesis of Imidazo[5,1-f][1,2,4]triazin-4(3H)-ones", J. Org. Chem. 2005, 70, 7331-7337.
Charles et al., "Bicyclic Heterocycles with Nitrogen at the Ring Junction. Part 2. Application of the Dakin-West Reaction to the Synthesis of Imidazo-[5,1-f]-1,2,4-triazin-4(3H)-ones", J.C.S. Perkin I, 1980, pp. 1139-1146.
Long et al., "The synthesis of a phosphodiesterase(V) inhibitor Vardenafil", School of Chemistry and Chemical Engineering, Shanghai Jiao Tong University, Shanghai 200240, China, Huaxue Shiji, Chemical Agent 2006. 28(5), pp. 287-289.

* cited by examiner

*Primary Examiner* — Susanna Moore
*Assistant Examiner* — Cecilia M Jaisle
(74) *Attorney, Agent, or Firm* — Carter, DeLuca, Farrell & Schmidt LLP

(57) ABSTRACT

Disclosed are N-{1-[3-(2-ethoxy-5-(4-ethylpiperazinyl)sulfonylphenyl)-4,5-dihydro-5-oxo-1,2,4-triazin-6-yl] ethyl}butyramide (which is represented by formula III and utilized for preparing vardenafil), its preparation method, intermediates during preparation procedure, preparation method for such intermediates and a method for preparing vardenafil from the compound. In the method for preparing vardenafil, a chloro-sulfonation reaction carries out in the early stage of the preparation procedure

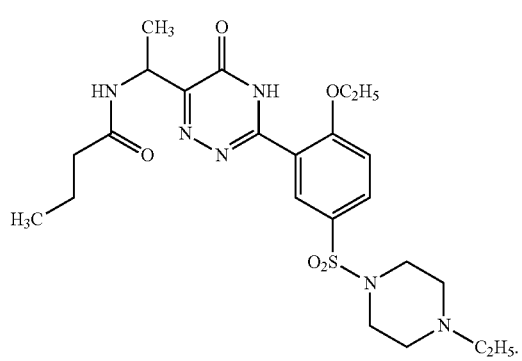

12 Claims, No Drawings

N-{1-[3-(2-ETHOXY-5-(4-ETHYLPIPERAZINYL) SULFONYLPHENYL)-4,5-DIHYDRO-5-OXO-1,2, 4-TRIAZIN-6-YL]ETHYL}BUTYRAMIDE, THE PREPARATION METHOD AND USE THEREOF

TECHNICAL FIELD

The present invention pertains to pharmaceutical field, specifically, relates to N-{1-[3-(2-ethoxy-5-(4-ethylpiperazinyl) sulfonylphenyl)-4,5-dihydro-5-oxo-1,2,4-triazin-6-yl] ethyl}butyramide (which is represented by formula III), its preparation method, and the method for preparing vardenafil from the compound.

BACKGROUND

Vardenafil (the active ingredient of levitra), which has a structure shown by the following formula:

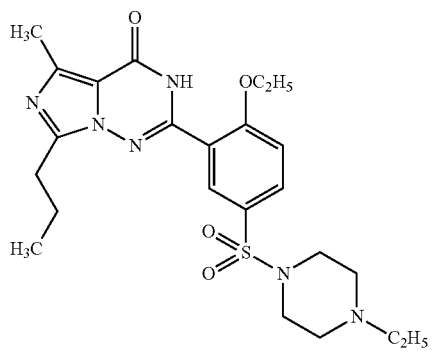

I and a chemical name of 2-[2-ethoxy-5-[(4-ethylpiperazin-1-yl)sulfonyl)phenyl]-5-methyl-7-propyl-imidazo[5,1-f][1,2,4]triazin-4-one, is a PDE5 selective inhibitor developed by Bayer Company (German) in 2001 to treat erectile dysfunction (ED) clinically.

International patent application WO 9924433 A1 first disclosed the above compound, its preparation method and uses thereof for treating ED. According to the process described in the above patent document, the last several reaction steps may be shown by the following scheme:

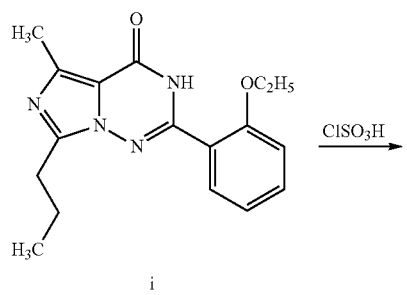

i

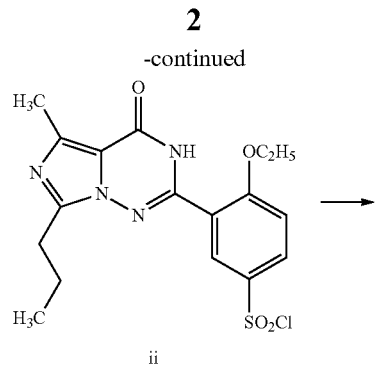

ii

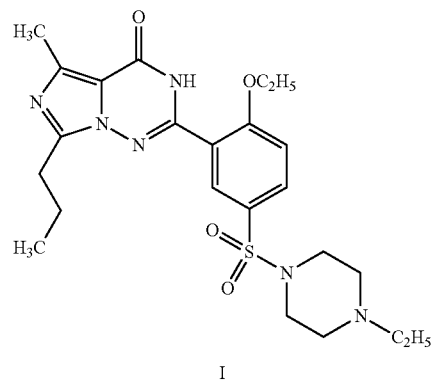

I

In the preparation method, in the late stage of preparation procedure, compound i was reacted with a high active agent, chlorosulfonic acid, to provide a water-sensitive chloro-sulfonated product ii, which was then reacted with an organic amine such as N-ethylpiperazine to give the target compound of formula I. However, it is difficult to achieve the industrialized production of the above compound by the above reaction routine. In the last stage of forming the product, the chloro-sulfonation needs consuming a large amount of chlorosulfonic acid, which prolongs the posttreatment time of the reaction, and in turn increases the amount of the impurity iii generated by the hydrolysis of the unstable intermediate (chloro-sulfonated product ii). The above hydrolysis is shown as follows:

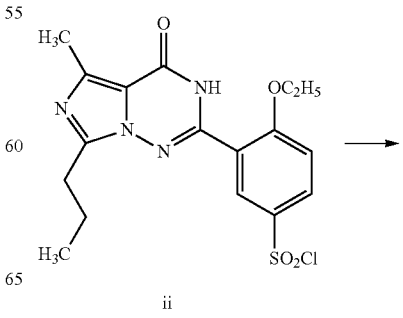

ii

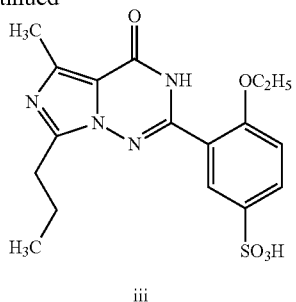

Therefore, it needs to increase the purification time of the final product so as to meet the request for the quality of a pharmaceutical acceptable active ingredient. Therefore, in the last stage of the preparation procedure of the above process, the chloro-sulfonation not only decreases the final yield of the aimed product, but also increases the purification time of the aimed product.

International patent application WO 200250076 provided a modification to the above process so as to be more suitable for a large scale manufacture. The key steps of the modified process are shown as follows:

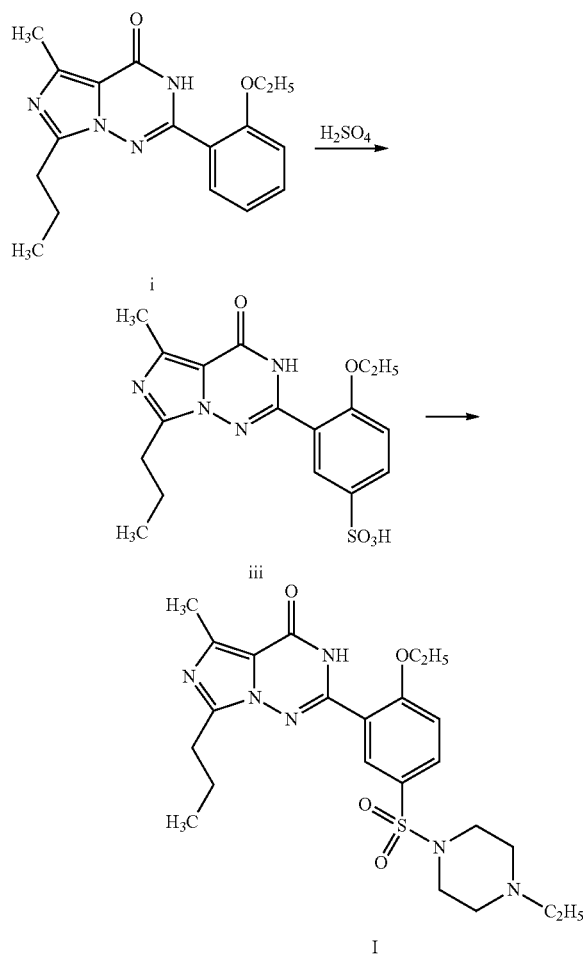

The process introduced a sulfonic acid group into the benzene ring by using concentrated sulfuric acid to obtain the compound iii, which was then converted into the chloro-sulfonated product ii by using thionyl chloride. The replacement of chlorosulfonic acid used in the original process with thionyl chloride increased the yield of the reaction, facilitating the production of the product. But similar to WO 9924433 A1, this process obtained the aimed product by reacting the chloro-sulfonated product ii, which is highly sensitive to water, with N-ethylpiperazine. Thus, during processing, it exists inevitably the side reaction wherein the generated intermediate ii is re-hydrolyzed to the impurity iii.

Although WO 200250075 and US 2006264624 sequentially disclosed new intermediates for vardenafil, and new preparation methods thereof, the above technical problem is not thoroughly solved. In the methods for preparing vardenafil reported in Journal of Organic Chemistry, 2005, 70(18): 7331-7337; organic Process Research & Development, 2005, 9(1), 88-97; and Chemical Agent, 2006, 28(5), 287-288, the above technical problem is also discussed.

SUMMARY OF THE INVENTION

The object of the present invention is to provide a new intermediate (i.e. the compound of formula III) for vardenafil, and a preparation method thereof, as well as a method for preparing vardenafil from the same.

The present invention provides a compound of the following formula III:

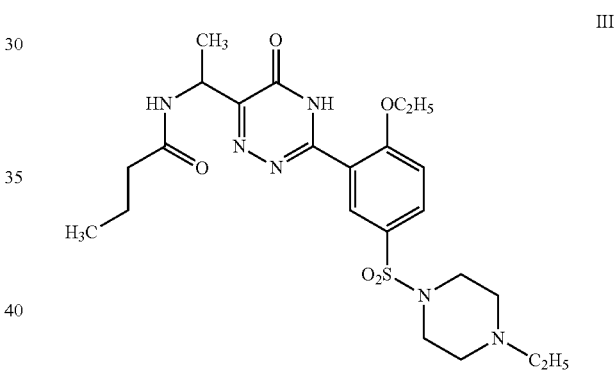

which has a chemical name of N-{1-[3-(2-ethoxy-5-(4-ethylpiperazinyl)sulfonylphenyl)-4,5-dihydro-5-oxo-1,2,4-triazin-6-yl]ethyl}butyramide.

The present invention further provides two methods for preparing the compound of formula III.

Method one: the compound of formula III may be obtained by reacting the compound of formula II with the compound of formula IV in an organic solvent. The reaction is shown by the following scheme:

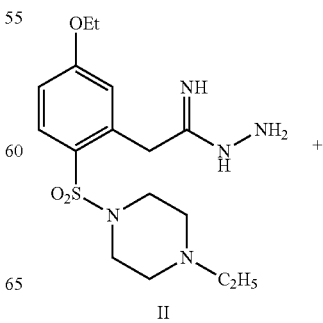

-continued

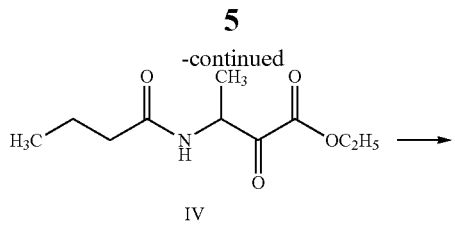

IV

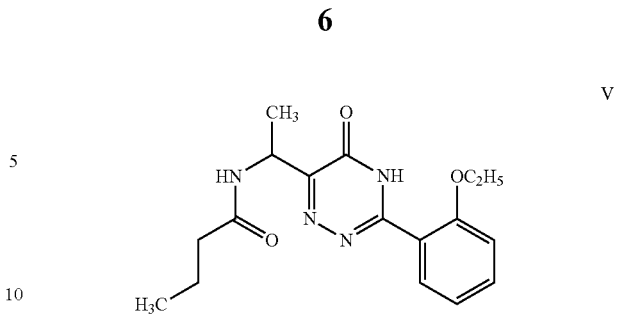

V

The temperature of the chloro-sulfonation is from −20° C. to 60° C., preferably from −5° C. to 5° C.

The chloro-sulfonation may be carried out in an organic solvent, such as dichloromethane, chloroform, ethyl acetate etc.

In the presence of an alkali, the organic solvent for the reaction of the chloro-sulfonated product and N-ethylpiperazine is selected from the group consisting of methanol, ethanol, n-propanol, isopropanol, n-butanol, ethyl ether, dioxane, tetrahydrofuran, ethylene glycol monomethyl ether, ethylene glycol dimethyl ether, dichloromethane, chloroform, carbon tetrachloride, dichloroethane, benzene, toluene, xylene, n-hexane, cyclohexane, ethyl acetate, acetonitrile, acetone, and N,N-dimethyl formamide, preferably from dichloromethane, chloroform, ethyl acetate, and acetone, and more preferably from dichloromethane.

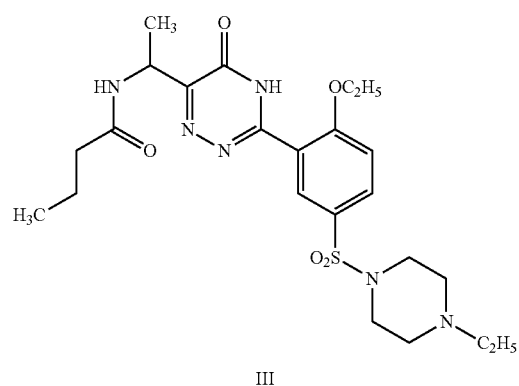

III

The organic solvent is selected from the group consisting of methanol, ethanol, n-propanol, isopropanol, n-butanol, ethyl ether, dioxane, tetrahydrofuran, ethylene glycol monomethyl ether, ethylene glycol dimethyl ether, dichloromethane, chloroform, carbon tetrachloride, dichloroethane, benzene, toluene, xylene, n-hexane, cyclohexane, ethyl acetate, acetonitrile, acetone, and N,N-dimethyl formamide, and preferably from the group consisting of methanol, ethanol, n-propanol, and isopropanol.

The reaction temperature is from 40° C. to 200° C., preferably from 50° C. to 80° C.

Among them, the compound of formula IV is a known compound, which may be prepared with reference to the process disclosed in J. Chem. Soc. Perkin Trans. 1; EN; 1980; 1139-1146, or by the Dakin-West reaction of the compound of formula VI with ethyl oxalyl monochloride:

The alkali used in the reaction is selected from the group consisting of organic amines, metal salts of an amine, hydroxides, carbonates, or bicarbonates. Preferably, the alkali is selected from the group consisting of triethylamine, sodium hydroxide, potassium hydroxide, sodium carbonate, potassium carbonate, sodium bicarbonate, and potassium bicarbonate, and more preferably from triethylamine, sodium carbonate and sodium bicarbonate.

The compound of formula V may be prepared with reference to Chemical Agent 2006, 28(5), 287-288 according to the following scheme.

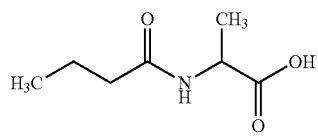

VI

The compound of formula VI in the present invention may be prepared according to a common process in organic chemistry by reacting ethyl oxalyl monochloride with D,L-aminopropionic acid.

Method two: the compound of formula III may also be obtained by chloro-sulfonating the compound of formula V with chlorosulfonic acid to provide the corresponding chlorosulfonated product, separating the chloro-sulfonated product, and then reacting the chloro-sulfonated product with N-ethylpiperazine in an organic solvent in presence of an alkali.

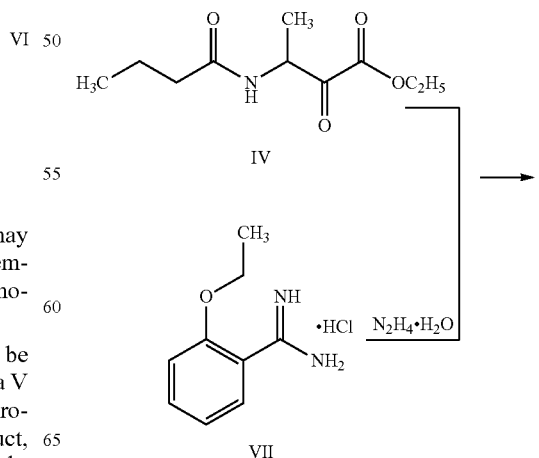

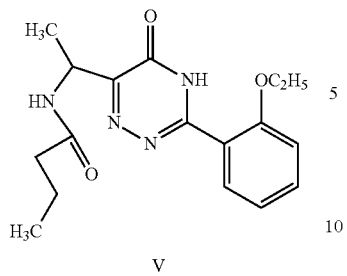

V

The compound of formula VII in the present invention may be prepared according to the process disclosed in J. Chem. Soc. Perkin Trans. 1; EN; 1980; 1139-1146.

The present invention further provides the compound of formula II or a salt thereof being as an intermediate for the compound of formula III.

II

Among others, the salt of the compound of formula II is preferably a hydrochloride, a sulfate, or a phosphate.

The present invention further provides a method for preparing the compound of formula II or a salt thereof, which may be implemented by the following scheme.

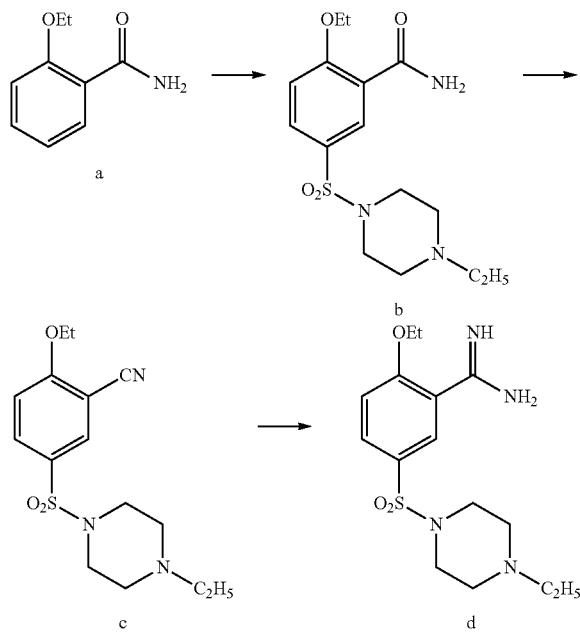

The specific steps of the method are as follows.

i. The compound of formula a reacts with chlorosulfonic acid to provide a corresponding chloro-sulfonated product, which is separated, and then reacts with N-ethylpiperazine to form the compound of formula b.

Excess chlorosulfonic acid may be added as a reaction solvent into the reaction of the compound of formula a and chlorosulfonic acid. After completion of the reaction, the reaction mixture is poured into water, mixture of water and ice, or chopped ice, and the solid was separated by vacuum filtration and recrystallized to afford a chloro-sulfonated product, which then reacts with N-ethylpiperazine to provide the compound of formula b. Alternatively, after the reaction mixture is poured into water, mixture of water and ice, or chopped ice, the chloro-sulfonated product is obtained through extraction by using an organic solvent, such as dichloromethane, chloroform, ethyl acetate, etc. The chloro-sulfonation may also be performed by adding 1-10 mole equivalent chlorosulfonic acid into an organic solvent, such as dichloromethane, chloroform, ethyl acetate, etc, pouring the reaction mixture into water, mixture of water and ice, or chopped ice after completion of reaction, separating the liquid to obtain a solution containing the chloro-sulfonated product, and directly adding methylpiperazine into the solution.

For reducing cost, in the process of the present invention, after the chloro-sulfonated product is extracted, 1.5 mole equivalents N-ethylpiperazine is directly added thereinto to perform the reaction, followed by purification to give the compound of formula b. The reaction may be carried out at a temperature within a specific range of, typically from −10° C. to 50° C., and preferably from −5° C. to 30° C.

Among them, the compound of formula a is a known compound, which may be obtained according to various processes in organic chemistry.

ii. The compound of formula b reacts with POCl$_3$ to give the compound of formula c:

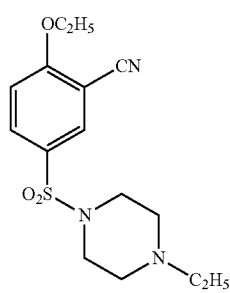

c

In the above reaction, POCl$_3$ may be used in an excess amount selected from 1-20 mole equivalents. The reaction temperature is from 40° C. to 120° C., preferably, from 60° C. to 120° C. After completion of reaction, the reaction is quenched by ice water, PH value is adjusted to 6-9, and the solid is separated by vacuum filtration, or the compound of formula c is obtained through extraction by using an organic solvent.

iii. The compound of formula c reacts with Li[NSi(CH$_3$)$_3$]2 to provide the compound of formula d:

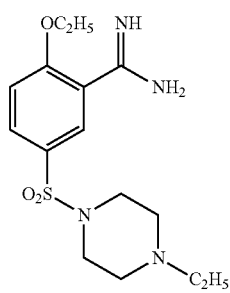

d

There are a lot of ways to convert the compound of formula c into the compound of formula d. In the process of the present invention, the above conversion is achieved by using Li[NSi(CH$_3$)$_3$]2. The reaction solvent may be tetrahydrofuran, and Li[NSi(CH$_3$)$_3$] may be used in an amount of 1-5 mole equivalents. The reaction temperature is within the range of −20° C. to 40° C.

iv. The compound of formula d or a salt thereof is treated with hydrazine hydrate in an organic solvent to obtain the compound of formula II or a salt thereof.

The salt of the compound of formula d may be a hydrochloride, a sulfate, or a phosphate, etc.

The compound of formula d or a salt thereof is dissolved into an organic solvent, followed by adding thereinto hydrazine hydrate to be converted into the compound of formula II or a salt thereof at a temperature ranging from −20° C. to 40° C. The organic solvent may be selected from a group consisting of methanol, ethanol, n-propanol, isopropanol, and n-butanol, preferably from ethanol, methanol, and n-propanol.

The salt of the compound of formula II may be a hydrochloride, a sulfate, or a phosphate, etc.

The present invention further provides a method for preparing the compound of formula I from the compound of formula III, which is implemented by the following scheme.

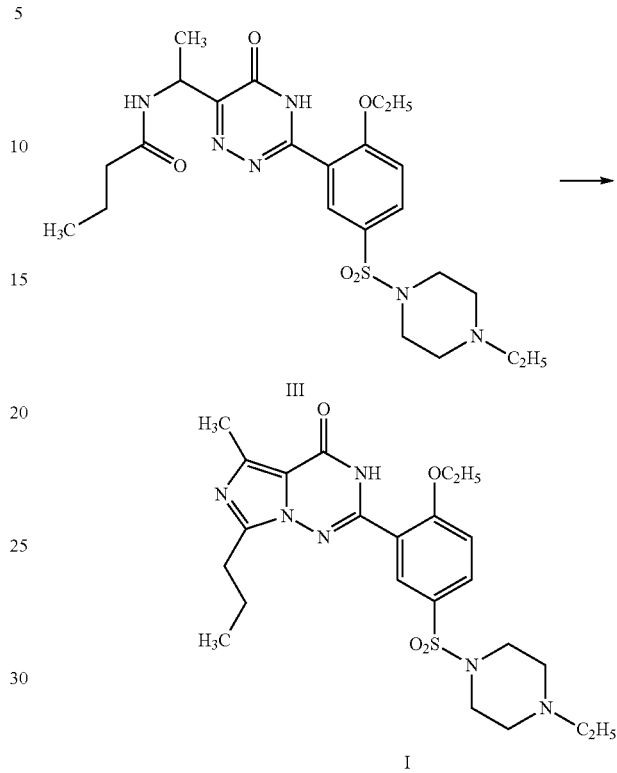

The compound of formula I is obtained by cyclizing the compound of formula III in the presence of phosphorous oxychloride, or phosphorous oxychloride and acetic acid. The specific steps are as follows. The compound of formula III is treated with phosphorous oxychloride, or phosphorous oxychloride and acetic acid at a temperature ranging from 40° C. to 120° C. After completion of reaction, the excess phosphorous oxychloride, or phosphorous oxychloride and acetic acid are removed by evaporation under reduced pressure, and the residue is poured into water, mixture of ice and water, or chopped ice. The chemical compound of formula I is obtained through extraction by using an organic solvent selected from a group consisting of dichloromethane, chloroform, and ethyl acetate.

In addition, it needs to be particularly indicated that after the compound of formula III is obtained by reacting the compound of formula II and the compound of formula IV in a solvent, it may be treated with phosphorous oxychloride, or phosphorous oxychloride and acetic acid without purification to afford the compound of formula I. Specifically, the chemical compound of formula II and the chemical compound of formula IV are heated in an alcohol organic solvent to provide the chemical compound of formula III, which, after the solvent is removed by evaporation, is directly treated with phosphorous oxychloride, or phosphorous oxychloride and acetic acid to give the chemical compound of formula I. The alcohol solvent used in the reaction may be selected from a group consisting of methanol, ethanol, n-propanol, isopropanol, and tert-butanol. The reaction temperature is from 40° C. to 200° C., preferably from 50° C. to 80° C.

The method for preparing vardenafil from the compound of formula III according to the present invention eliminates the defect of those in the prior art that the chloro-sulfonation is carried out in the last stage of the preparation procedure, thereby resulting in the easy occurrence of hydrolysis to generate the impurity iii. The method for preparing vardenafil from the compound of formula III according to the present invention reduces the amount of the highly poisonous and dangerous substance, chlorosulfonic acid, used in the reaction by performing the chloro-sulfonation in the early stage of the preparation procedure, which is due to the fact that the compound in the early stage of preparation procedure has a relative small molecular weight, and thereby consumes a relatively small amount of chlorosulfonic acid to obtain the same mole, or same mass of the final product, in comparison with the chloro-sulfonation carried out in the last stage of preparation procedure. In addition, the reduction in the amount of chlorosulfonic acid not only shortens the post processing time of the reaction and lowers the probability for occurring the side reaction, but also may greatly decrease the cost for treating the waste water generated by using chlorosulfonic acid, thereby reducing the extent and possibility of harm to environment. Furthermore, the impurity, which is introduced into the final product due to the side reaction, is reduced by preparing vardenafil from the chloro-sulfonated compound of formula III, thus greatly decreasing the difficulty of purification of the product and lowering the cost for preparing the product.

BEST MODE FOR CARRYING OUT THE INVENTION

The present invention will be further illustrated through the following examples, which, however, are intended only to illustrate the preferred mode for carrying out the invention, and may not be construed to limit the technical solutions of the present invention. All of the above technical solutions of the present invention are those enable to realize the object of the present invention. That is to say, the temperatures and chemical agents adopted in the following examples may be replaced by the corresponding temperatures and chemical agents described above to realize the invention.

The solvents or chemical agents used in the experiments were all produced by the Chemical Agent Ltd. of the State Medicine Group. The melting point was measured on a melting point detector (mode: BUCHI-510) with a uncalibrated temperature. The mass spectra were recorded on a MAT-95 mass spectrometer and a Finnigan SW01-0002 mass spectrometer. $^1$H nuclear magnetic resonance spectra were measured by a Varian Mercury 300 instrument. All spectra were in conformity with the structures inferred, and the characterized peaks were expressed by the normal abbreviation: s, single peak; d, dual peaks; t, triple peaks; q, quadri peaks; m, multiple peaks.

The room temperature means a temperature ranging from 20° C. to 25° C.

EXAMPLE 1

Preparation Example 1

Preparation of 2-butyramido propionic acid (VI)

D,L-aminopropionic acid (20.0 g, 0.225 mol) was added into a mixture of water (100 mL) and acetone (50 mL), followed by addition of NaOH (22.5 g, 0.225 mol) therein to obtain a clear solution. n-butyryl chloride (26.4 mL, 0.248 mol) was slowly dropped therein under an ice-salt bath. After the dropping, the temperature was kept below 5° C. and the reaction was carried out for 2 hours. The ice bath was removed, and acetone was evaporated off under reduced pressure. The PH value was adjusted to 1.0 by a 6 mol/L hydrochloric acid, and ethyl acetate (100 mL×3) was added therein. After water separated and dried, ethyl acetate was evaporated off to afford a light yellow oil, into which was added a suitable amount of petroleum ether to precipitate a white solid. The white solid was vacuum-filtered and dried to give the product VI (25.8 g) with a yield of 72%. $^1$H NMR (CDCl$_3$, 300 MHz) δ: 0.94 (3H, t), 1.44 (3H, d), 1.65 (2H, m), 2.22 (2H, t), 4.57 (2H, m), 6.37 (1H, d), 6.62 (1H, s).

Preparation Example 2

Preparation of ethyl 3-butyramido-2-oxo-butyrate (IV)

The compound of formula VI (3.18 g, 0.02 mol) was dissolved into dried tetrahydrofuran (20 mL), followed by addition of DMAP (0.08 g, 0.6 mmol) and pyridine (5 mL) therein. The mixture was heated for 30 minutes at 50° C., and then cooled. Under ice bath, ethyl oxalyl monochloride (5.46 g, 0.04 mol) was slowly dropped therein. After the dropping, the mixture was heated for 4 hours at 70° C. The solid was filtered off and the solvent was evaporated off under reduced pressure. Water (40 mL) was added therein, and the product was extracted by using ethyl acetate (75 mL×3). The liquid was separated, and the combined organic phase was washed by water (30 mL) and saturated saline (30 mL×2) respectively, and dried over anhydrous sodium sulfate. After the solvent therein was removed by rotary evaporation, NaHCO$_3$ (1.26 g, 0.015 mol) and methanol (20 mL) were added therein, and the mixture was refluxed for 2 hours. After filtration, the solvent was removed by evaporation under reduced pressure to give a yellow oil, i.e., ethyl 3-butyramido-2-oxo-butyrate, which is directly used in the next step without purification.

Preparation Example 3

Preparation of N-{1-[3-(2-ethoxyphenyl)-4,5-dihydro-5-oxo-1,2,4-triazin-6-yl]ethyl}butyramide (V)

o-ethoxybenzamidine hydrochloride (VII) (2.01 g, 10 mmol) was dissolved into ethanol (15 ml), and 85% hydrazine hydrate (0.59 mL, 10 mmol) was slowly dropped therein under an ice bath. After the dropping, the reaction mixture reacted for 30 minutes under ice bath, and then stirred for 1 hour at room temperature, followed by addition of a solution of the product (2.58 g) obtained in preparation example 2 in ethanol (15 mL). The reaction mixture was heated to reflux for 3 hours, and filtered off the solid. The filtrate was concentrated to obtain an oil, which then passed through silica gel column eluting with a mixture of petroleum ether:ethyl acetate=2:3 to finally obtain a light yellow solid (1.98 g), i.e., the compound of formula V, with a yield of 60%. $^1$H NMR (CDCl$_3$, 300 MHz) δ: 0.92 (3H, t), 1.52 (3H, d), 1.59 (3H, t), 1.65 (2H, m), 2.17 (2H, t), 4.34 (2H, q), 5.24 (1H, m), 6.94 (1H, d), 7.06 (1H, d), 7.14 (1H, t), 7.55 (1H, dt), 8.55 (1H, dd), 12.44 (1H, s). EI-MS m/z 330 (M$^+$, 37), 331 (8), 287 (10), 259 (100), 217 (36), 91 (8).

Preparation Example 4

Preparation of N-{1-[3-(2-ethoxy-5-(4-ethylpiperazinyl)sulfonylphenyl)-4,5-dihydro-5-oxo-1,2,4-triazin-6-yl]ethyl}butyramide (III)

The compound (0.66 g, 2 mmol) of formula V was added into chlorosulfonic acid (1 mL) under an ice-salt bath in batches, and the mixture was reacted under the ice-salt bath for half hour, and then stirred for 1 hour at room temperature. The reactant liquid was slowly dropped into chopped ice, and extracted with dichloromethane (50 mL). The organic phase was washed with saturated saline (20 mL), and was charged immediately with N-ethylpiperazine (0.46 g, 4 mmol). The reaction mixture was reacted for half hour below 5° C., and then stirred for 30 minutes at room temperature. Distilled water (20 mL) was added therein to separate the liquid, and the organic phase was washed with saturated aqueous ammonium chloride solution (15 mL×2) and saturated saline (15 mL). The solvent was evaporated off to afford 0.78 g of a light yellow solid, i.e., the compound of formula III, with a yield of 77%. $^1$H NMR (CDCl$_3$, 300 MHz) δ: 0.93 (3H, t), 1.02 (3H, t), 1.53 (3H, d), 1.63 (3H, t), 1.66 (2H, m), 2.19 (2H, t), 2.44 (2H, q), 2.54 (4H, t), 3.06 (4H, t), 4.42 (2H, q), 5.26 (1H, m), 6.85 (1H, d), 7.18 (1H, d), 7.90 (1H, dd), 8.84 (1H, d), 12.32 (1H, s). EI-MS m/z 506 (M$^+$, 5), 450 (56), 420 (40), 113 (100), 70 (8).

Preparation Example 5

Preparation of 2-[2-ethoxy-5-[(4-ethyl-1-piperazinyl) sulfonyl]phenyl]-5-methyl-7-propyl-imidazo[5,1-f] [1,2,4]triazin-4-one (I)

The compound of formula III (0.51 g, 1 mmol) was added with POCl$_3$ (2 mL), and the mixture was heated for 2 hours at 80° C. The excess phosphorous oxychloride was evaporated of under reduced pressure, and the residue was slowly poured into chopped ice. The solution was adjusted to a pH of 8 with sodium carbonate, and extracted with dichloromethane (40 mL). The organic phase was washed with saturated saline (15 mL), and dried over anhydrous sodium sulfate. Then, 20 mL of ethanol was added therein, and the solution was decolorized by activated carbon, filtrated, and evaporated to remove some of the solvent therefrom. Ethyl acetate was then added therein to perform a recrystallization. Finally, the crystal was separated to obtain 0.32 g of product with a yield of 65%. $^1$H NMR (CDCl$_3$, 300 MHz) δ: 1.01 (3H, t), 1.04 (3H, t), 1.62 (3H, t), 1.86 (2H, m), 2.42 (2H, q), 2.54 (4H, t), 2.64 (3H, s), 2.99 (2H, t), 3.07 (4H, m), 4.34 (2H, q), 7.15 (1H, d), 7.88 (1H, dd), 8.48 (1H, d), 9.52 (1H, s).

EXAMPLE 2

Preparation Example 1

Preparation of 2-ethoxy-5-(4-ethylpiperazin-1-yl-sulfonyl)benzamide (b)

Orthoethoxybenzamide (33.0 g, 0.20 mol) was added into a mixture of chlorosulfonic acid (60 mL) and thionyl chloride (20 mL) cooled by an ice bath in batches, and the temperature of the reaction system was kept below 20° C. After the completion of reaction identified by TLC, the reactant liquid was poured into chopped ice to separate a white solid. The product was extracted out with dichloromethane (200 mL), and N-ethylpiperazine (45.6 g, 0.40 mol) was added therein under an ice bath. The reaction mixture was reacted for 30 minutes under an ice bath, and then stirred for 1 hour at room temperature. Water (10 mL) was added therein to separate the liquid, and the organic phase was washed with saturated aqueous ammonium chloride solution (100 mL), dried over anhydrous sodium sulfate, and concentrated to 50 mL. Petroleum ether (100 mL) was dropped therein to separate a white acicular crystal, 58.6 g, and the final product was obtained by vacuum filtration with a yield of 86%. $^1$H NMR (CDCl$_3$, 300 MHz) δ: 1.01 (3H, t), 1.56 (3H, t), 2.38 (2H, q), 2.50 (4H, t), 3.03 (4H, t), 4.28 (2H, q), 6.14 (1H, s), 7.06 (1H, d), 7.67 (1H, s), 7.82 (1H, dd), 8.58 (1H, d).

Preparation Example 2

Preparation of 2-ethoxy-5-(4-ethylpiperazin-1-yl-sulfonyl) cyanophenyl (c)

The compound of formula b (51.2 g, 0.15 mol) was slowly added into POCl$_3$ (100 mL), and the reaction mixture was refluxed for 1 hour. The excess POCl$_3$ was removed by evaporation under reduced pressure, and the obtained residue was slowly poured into chopped ice to separate a white solid. The PH was adjusted to 6, and the separated solid was vacuum-filtrated off and dried. Ethyl acetate was then added therein to perform a recrystallization to obtain 40.3 g of a white acicular crystal with a yield of 83%. $^1$H NMR (CDCl$_3$, 300 MHz) δ: 1.47 (3H, t), 1.54 (3H, t), 2.97 (2H, q), 3.10 (2H, m), 3.37 (2H, t), 3.55 (2H, d), 3.87 (2H, d), 4.26 (2H, q), 7.10 (1H, d), 7.85 (1H, dd), 7.96 (1H, d).

Preparation Example 3

Preparation of 2-ethoxy-5-(4-ethylpiperazin-1-yl-sulfonyl)benzamidine (d)

The compound of formula c (32.3 g, 0.1 mol) was slowly dropped into a 20% solution of LiN[Si(CH$_3$)$_3$]$_2$ in tetrahydrofuran (200 mL) under nitrogen, and the mixture was stirred for 30 minutes under an ice bath, and then reacted for 9 hours at room temperature. The mixture was adjusted to a pH of 3 with 1 mol/L diluted hydrochloric acid, evaporated under reduced pressure to remove tetrahydrofuran, and then adjusted to a pH of 12 by a 2 mol/L solution of sodium hydroxide to separate a white solid. The solid was vacuum-filtrated and dried to obtain 27.8 g of final product with a yield of 83%. $^1$H NMR (CDCl$_3$, 300 MHz) δ: 1.02 (3H, t), 1.49 (3H, t), 2.40 (2H, q), 2.52 (4H, t), 3.03 (41-1, t), 4.18 (2H, q), 7.02 (1H, d), 7.74 (1H, dd), 7.94 (1H, d). ESI-MS m/z 341.2 (M$^+$+1, 100).

Preparation Example 4

Preparation of 2-ethoxy-5-(4-ethylpiperazin-1-yl-sulfonyl)-N-amino-benzamidine

The compound of formula d (17.2 g, 0.05 mol) was dissolved in ethanol (100 ml), and 85% hydrazine hydrate (2.9 g, 0.05 mmol) was slowly dropped into the solution under ice bath. The mixture was stirred for 30 minutes and then at room temperature for 1 hour. After the solution was concentrated to 30 mL, a solid was filtrated out, washed with ethyl acetate, and dried under vacuum to obtain 13.8 g of product with a yield of 78%. $^1$H NMR (CDCl$_3$, 300 MHz) δ: 1.02 (3H, t), 1.49 (3H, t), 2.39 (2H, q), 2.51 (4H, t), 3.05 (4H, t), 4.18 (2H, q), 7.00 (1H, d), 7.69 (1H, dd), 8.13 (1H, d). ESI-MS m/z 356.3 (M$^+$+1, 100).

Preparation Example 5

Preparation of ethyl 3-butyramido-2-oxo-butyrate (IV)

The compound of formula VI (9.54 g, 0.06 mol) was dissolved into dried tetrahydrofuran (60 mL), and DMAP (0.24 g, 2.0 mmol) and pyridine (15 mL) were added therein. The mixture was heated for 30 minutes at 50° C., cooled, and slowly dropped with ethyl oxalyl monochloride (16.4 g, 0.12 mol) under an ice bath. After the dropping, the mixture was heated for 4 hours at 70° C., filtered to remove the solid, and evaporated to remove the solvent under reduced pressure. Water (100 mL) was added therein, and the product was extracted with ethyl acetate (120 mL×3). The liquid was separated, and the combined organic phase was washed by water (90 mL) and saturated saline (50 mL×2) respectively, dried over anhydrous sodium sulfate, and rotarily evaporated to remove the solvent. NaHCO$_3$ (3.8 g, 0.045 mol) and methanol (50 mL) were added therein, and the reaction mixture was refluxed for 2 hours, filtered, and evaporated off the solvent under reduced pressure to obtain a yellow oil, i.e., ethyl 3-butyramido-2-oxo-butyrate, which was directly used in the next step without separation.

Preparation Example 6

Preparation of N-{1-[3-(2-ethoxy-5-(4-ethylpiperazinyl)sulfonylphenyl)-4,5-dihydro-5-oxo-1,2,4-triazin-6-yl]ethyl}butyramide (III)

The product obtained in the preparation example 5 of the example 2 was dissolved into ethanol (120 ml), and the compound of formula II (14.2 g, 0.04 mol) was added therein. The reaction mixture was refluxed for 2 hours, filtrated to remove the solid, and evaporated off the solvent therein under reduced pressure to obtain an oil, which was then passed through a silica gel column to obtain 14.5 g of product with a yield of 71.6%. $^1$H NMR (CDCl$_3$, 300 MHz) δ: 0.93 (3H, t), 1.02 (3H, t), 1.53 (3H, d), 1.63 (3H, t), 1.66 (2H, m), 2.19 (2H, t), 2.44 (2H, q), 2.54 (4H, t), 3.06 (4H, t), 4.42 (2H, q), 5.26 (1H, m), 6.85 (1H, d), 7.18 (1H, d), 7.90 (1H, dd), 8.84 (1H, d), 12.32 (1H, s). EI-MS m/z 506 (M$^+$, 5), 450 (56), 420 (40), 113 (100), 70 (8).

Preparation Example 7

Preparation of 2-[2-ethoxy-5-[(4-ethyl-1-piperazinyl)sulfonyl]phenyl]-5-methyl-7-propyl-imidazo[5,1-f][1,2,4]triazin-4-one (I)

The compound of formula III (0.51 g, 1 mmol) was added with POCl$_3$ (2 mL), and the mixture was heated for 2 hours at 80° C. The excess phosphorous oxychloride was removed by evaporation under reduced pressure, and the residue was slowly poured into chopped ice. The solution was adjusted to a pH of 8 with sodium carbonate, extracted with dichloromethane (40 mL), washed by saturated saline (15 mL), and dried over anhydrous sodium sulfate. Then, 20 mL of ethanol was added therein, and the solution was decolorized by activated carbon, filtrated, and evaporated to remove the solvent. Ethyl acetate was then added therein to perform a recrystallization, and the crystal was separated to obtain 0.32 g of product with a yield of 65%. $^1$H NMR (CDCl$^3$, 300 MHz) δ: 1.01 (3H, t), 1.04 (3H, t), 1.62 (3H, t), 1.86 (2H, m), 2.42 (2H, q), 2.54 (4H, t), 2.64 (3H, s), 2.99 (2H, t), 3.07 (4H, m), 4.34 (2H, q), 7.15 (1H, d), 7.88 (1H, dd), 8.48 (1H, d), 9.52 (1H, s).

EXAMPLE 3

Preparation Example 1

Preparation of 2-ethoxy-5-(4-ethylpiperazin-1-yl-sulfonyl)benzamidine (d) hydrochloride The product obtained in the preparation example 3 of the example 2 (34 g, 0.1 mol), i.e. 2-ethoxy-5-(4-ethylpiperazin-1-yl-sulfonyl)benzamidine (d), was dissolved into ethanol (200 mL), and concentrated hydrochloric acid (9.1 mL) was dropped therein under an ice bath. The solution was concentrated to dryness to obtain the hydrochloride of 2-ethoxy-5-(4-ethylpiperazin-1-yl-sulfonyl)benzamidine (d). $^1$H NMR (CDCl$_3$, 300 MHz) δ: 1.02 (3H, t), 1.49 (3H, t), 2.40 (2H, q), 2.52 (4H, t), 3.03 (4H, t), 4.18 (2H, q), 7.02 (1H, d), 7.74 (1H, dd), 7.94 (1H, d). ESI-MS m/z 341.2 (M$^+$+1, 100).

Preparation Example 2

Preparation of 2-ethoxy-5-(4-ethylpiperazin-1-yl-sulfonyl)-N-amino-benzamidine (II) hydrochloride The 2-ethoxy-5-(4-ethylpiperazin-1-yl-sulfonyl)benzamidine hydrochloride prepared in the above preparation example 1 was dissolved into ethanol (200 ml), and 85% hydrazine hydrate (5.9 g, 0.1 mol) was slowly dropped into the solution under ice bath. The mixture was stirred for 30 minutes and then at room temperature for 1 hour. Then, the solution was concentrated to dryness, and added with ethyl acetate to perform a recrystallization. The separated crystal was dried under vacuum to obtain 28 g of product with a yield of 74%. $^1$H NMR (CDCl$_3$, 300 MHz) δ: 1.02 (3H, t), 1.49 (3H, t), 2.39 (2H, q), 2.51 (4H, t), 3.05 (4H, t), 4.18 (2H, q), 7.00 (1H, d), 7.69 (1H, dd), 8.13 (1H, d). ESI-MS m/z 356.3 (M$^+$+1, 100).

Preparation Example 3

Preparation of ethyl 3-butyramido-2-oxo-butyrate (IV)

The compound of formula VI (3.18 g, 0.02 mol) was dissolved into dried tetrahydrofuran (20 mL), and DMAP (0.08 g, 0.6 mmol) and pyridine (5 mL) were added therein. The mixture was heated for 30 minutes at 50° C., cooled, and slowly dropped therein with ethyl oxalyl monochloride (5.46 g, 0.04 mol) under ice bath. After the dropping, the mixture was heated for 4 hours at 70° C., filtered to remove the solid, and evaporated under reduced pressure to remove the solvent. Water (40 mL) was added therein, and the solution was extracted with ethyl acetate (75 mL×3). The liquid was separated, the combined organic phase was washed with water (30 mL) and saturated saline (30 mL×2) respectively, dried over anhydrous sodium sulfate, and rotarily evaporated to remove the solvent therein. NaHCO$_3$ (1.26 g, 0.015 mol) and methanol (20 mL) were added therein, and the mixture was refluxed for 2 hours, filtered, and evaporated under reduced pressure to remove solvent to obtain a yellow oil, i.e., ethyl 3-butyramido-2-oxo-butyrate, which was directly used in the next step without separation.

Preparation Example 4

Preparation of N-{1-[3-(2-ethoxy-5-(4-ethylpiperazinyl)sulfonylphenyl)-4,5-dihydro-5-oxo-1,2,4-triazin-6-yl]ethyl}butyramide (III)

The product obtained in the preparation example 5 of the example 2 was dissolved into ethanol (30 ml), and the compound of formula II (7.83 g, 0.02 mol) was added therein. The mixture was refluxed for 2 hours, and filtered off the solid. The filtrate was concentrated to dryness to afford a crude product, which was directly used in the next step.

Preparation Example 5

Preparation of 2-[2-ethoxy-5-[(4-ethyl-1-piperazinyl)sulfonyl]phenyl]-5-methyl-7-propyl-imidazo[5,1-f][1,2,4]triazin-4-one (I)

The crude product obtained in the preparation example 4 was added with POCl$_3$ (30 mL), and the mixture was heated for 2 hours at 80° C. The excess phosphorous oxychloride was removed by evaporation under reduced pressure, and the residue was slowly poured into chopped ice. The solution was adjusted to a pH of 8 with a saturated solution of sodium carbonate, and extracted with dichloromethane (100 mL). The organic phase was washed with saturated saline (40 mL), and dried over anhydrous sodium sulfate, followed by addition of 40 mL ethanol. The solution was decolorized with activated carbon, filtrated, and evaporated to remove some of the solvent. Ethyl acetate was then added therein to perform a recrystallization, the crystal was separated to obtain 6.25 g of product with a yield of 64%. $^1$H NMR (CDCl$_3$, 300 MHz) δ: 1.01 (3H, t), 1.04 (3H, t), 1.62 (3H, t), 1.86 (2H, m), 2.42 (2H, q), 2.54 (4H, t), 2.64 (3H, s), 2.99 (2H, t), 3.07 (4H, m), 4.34 (2H, q), 7.15 (1H, d), 7.88 (1H, dd), 8.48 (1H, d), 9.52 (1H, s).

EXAMPLE 4

Preparation of 2-[2-ethoxy-5-[(4-ethyl-1-piperazinyl)sulfonyl]phenyl]-5-methyl-7-propyl-imidazo[5,1-f][1,2,4]triazin-4-one (I)

The crude product obtained in the preparation example 4 of the example 3 was added with acetic acid (25 mL) and POCl$_3$ (5 mL). The mixture was heated for 3 hours at 60° C., and the excess phosphorous oxychloride and acetic acid were removed by evaporation under reduced pressure. The residue was slowly poured into chopped ice, and the solution was adjusted to a pH of 8 with a saturated solution of sodium carbonate and extracted with dichloromethane (100 mL). The organic phase was washed with saturated saline (40 mL), and dried over anhydrous sodium sulfate, followed by addition of 40 mL ethanol. The solution was decolorized with activated carbon, filtered, and evaporated to remove some of the solvent. Ethyl acetate was then added therein to perform a recrystallization, and the crystal was separated to obtain 6.0 g of product. $^1$H NMR (CDCl$_3$, 300 MHz) δ: 1.01 (3H, t), 1.04 (3H, t), 1.62 (3H, t), 1.86 (2H, m), 2.42 (2H, q), 2.54 (4H, t), 2.64 (3H, s), 2.99 (2H, t), 3.07 (4H, m), 4.34 (2H, q), 7.15 (1H, d), 7.88 (1H, dd), 8.48 (1H, d), 9.52 (1H, s).

What is claimed is:

1. The compound of the following formula III:

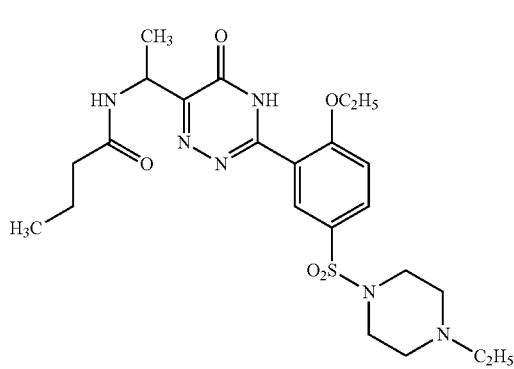

which has a chemical name of N-{1-[3-(2-ethoxy-5-(4-ethylpiperazinyl)sulfonylphenyl)-4,5-dihydro-5-oxo-1,2,4-triazin-6-yl]ethyl}butyramide.

2. A method for preparing the compound of formula III of claim 1, wherein the compound of formula III is obtained by reacting the compound of the following formula II or a salt thereof with the compound of the following formula IV in an organic solvent:

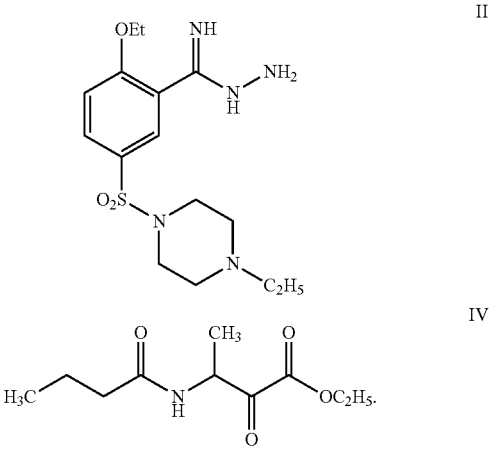

3. A method for preparing the compound of formula III according to claim 2, wherein the organic solvent is selected from the group consisting of methanol, ethanol, n-propanol, isopropanol, n-butanol, ethyl ether, dioxane, tetrahydrofuran, ethylene glycol monomethyl ether, ethylene glycol dimethyl ether, dichloromethane, chloroform, carbon tetrachloride, dichloroethane, benzene, toluene, xylene, n-hexane, cyclohexane, ethyl acetate, acetonitrile, acetone, and N,N-dimethyl formamide.

4. A method for preparing the compound of formula III according to claim 2, wherein a process for preparing the compound of formula II includes the following steps:

i. the compound of the following formula a reacts with chlorosulfonic acid; after completion of reaction, the reaction mixture is poured into water, a mixture of water and ice, or chopped ice, and filtered or extracted with an organic solvent to give a chloro-sulfonated product a-1, which is then reacted with N-ethylpiperazine to form the compound of the following formula b:

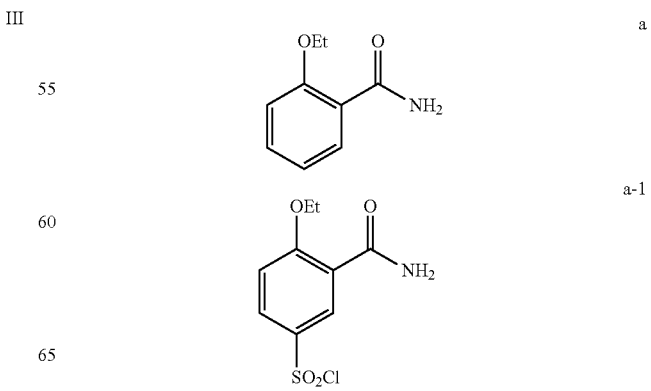

-continued b

[Structure of compound b: benzamide with OEt, NH2, and sulfonyl-piperazine-ethyl group]

ii. the compound of formula b reacts with POCl$_3$ to provide the compound of the following formula c:

c

[Structure of compound c: benzene with OC$_2$H$_5$, CN, and sulfonyl-piperazine-ethyl group]

iii. the compound of formula c reacts with the chemical agent Li[NSi(CH$_3$)$_3$]$_2$ to provide the compound of the following formula d:

d

[Structure of compound d: amidine with OC$_2$H$_5$ and sulfonyl-piperazine-ethyl group]

iv. the compound of formula d is treated with hydrazine hydrate in an organic solvent to provide the compound of formula II.

5. A method for preparing the compound of formula III according to claim 4, wherein, in the step iv of the process for preparing the compound of formula II, the organic solvent is selected from methanol, ethanol, n-propanol, isopropanol, and n-butanol.

6. A method for preparing the compound of formula III of claim 1, wherein the compound of formula III is obtained by chloro-sulfonating the compound of the following formula V with chlorosulfonic acid to obtain a chloro-sulfonated product V-1, separating the chloro-sulfonated product, and reacting the chloro-sulfonated product with N-ethylpiperazine in an organic solvent in presence of an alkali, selected from the group consisting of organic amines, metal salts of an amine, hydroxides, carbonates and bicarbonates,

V

[Structure of compound V]

V-1

[Structure of compound V-1 with SO$_2$Cl group]

7. A method for preparing the compound of formula III according to claim 6, wherein the chloro-sulfonation may be carried out in dichloromethane, chloroform, or ethyl acetate.

8. A method for preparing the compound of formula III according to claim 6, wherein the organic solvent is selected from the group consisting of methanol, ethanol, n-propanol, isopropanol, n-butanol, ethyl ether, dioxane, tetrahydrofuran, ethylene glycol monomethyl ether, ethylene glycol dimethyl ether, dichloromethane, chloroform, carbon tetrachloride, dichloroethane, benzene, toluene, xylene, n-hexane, cyclohexane, ethyl acetate, acetonitrile, acetone, and N,N-dimethyl formamide.

9. A method for preparing vardenafil from the compound of formula III of claim 1, wherein the vardenafil of formula I is obtained by cyclizing the compound of formula III in the presence of phosphorous oxychloride, or a mixture of phosphorous oxychloride and acetic acid,

I

[Structure of vardenafil formula I]

10. A method for preparing vardenafil according to claim 9, wherein the vardenafil of formula I of claim 9 is obtained by reacting the compound of formula III in the presence of phosphorous oxychloride, or a mixture of phosphorous oxychloride and acetic acid at a temperature ranging from 40 °C. to 120 °C.; after completion of reaction, evaporating the excess phosphorous oxychloride, or phosphorous oxychloride and acetic acid under reduced pressure and obtaining a residual liquid; pouring the residual liquid into water, mixture of ice and water, or chopped ice to obtain a solution, and then extracting the solution by using an organic solvent.

11. A method for preparing vardenafil according to claim 10, wherein the organic solvent is selected from dichloromethane, chloroform, and ethyl acetate.

12. The method according to claim 2, wherein the salt of the compound of formula II is a hydrochloride, a sulfate, or a phosphate.

* * * * *